United States Patent [19]

Ono

[11] Patent Number: 5,116,994
[45] Date of Patent: May 26, 1992

[54] DEACYLATING AGENT AND DEACYLATING METHOD

[75] Inventor: Mitsunori Ono, Kanagawa, Japan

[73] Assignee: Fuji Photo Film Co., Ltd., Kanagawa, Japan

[21] Appl. No.: 509,826

[22] Filed: Apr. 17, 1990

[30] Foreign Application Priority Data

Apr. 19, 1989 [JP] Japan .................... 1-99225
Jul. 19, 1989 [JP] Japan .................... 1-186248

[51] Int. Cl.$^5$ .......................... C07D 257/04
[52] U.S. Cl. ...................... 548/251; 549/263; 552/625; 552/630; 560/45; 560/139; 560/145; 564/170; 525/332.2; 525/377
[58] Field of Search .............. 548/251; 549/263; 552/625, 630; 560/45, 139, 145; 564/170

[56] References Cited

U.S. PATENT DOCUMENTS

| | | | |
|---|---|---|---|
| 3,875,114 | 4/1975 | Swiger | 525/333.6 |
| 3,899,472 | 8/1975 | Aya et al. | 525/332.2 |
| 4,085,261 | 4/1978 | Patchornik et al. | 526/19 |
| 4,330,642 | 5/1982 | Gaul, Jr. et al. | 525/377 |
| 4,568,725 | 2/1986 | Boisson et al. | 525/332.2 |

OTHER PUBLICATIONS

*Tetrahedron Letters*, No. 8, pp. 643–646 (1974).
*Tetrahedron Letters*, vol. 30, No. 2, pp. 207–210 (1989).

*Primary Examiner*—Bernard Lipman
*Attorney, Agent, or Firm*—Sughrue, Mion, Zinn, Macpeak & Seas

[57] ABSTRACT

Deacylating agent represented by the formula (I):

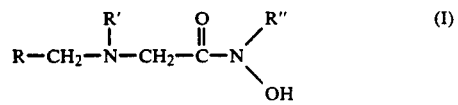

wherein R represents an insoluble polymer substituent, and R' and R'' each represents an alkyl group, and a deacylation method using the above deacylating agent.

6 Claims, 2 Drawing Sheets

DEACYLATING AGENT AND DEACYLATING METHOD

FIELD OF THE INVENTION

The present invention relates to a deacylating agent. More particularly, the present invention relates to a deacylating agent comprising an N-methyl-α-dialkylaminoacetohydroxamic acid compound immobilized onto a polymer bead.

BACKGROUND OF THE INVENTION

The deacylation of esters is performed in various fields. For example, it is used in releasing a photographic reagent from a photographic reagent precursor to be used in a silver halide photographic material, or in releasing a protective group in the synthesis of medicines.

In the cleavage of esters, a hydrolyzing method using hydroxy ions ($\ominus$OH) or hydrogen ions (H$\oplus$) is usually employed. However, when a molecule contains two or more acyl groups and only one of them is to be selectively cleaved, or when a compound or a functional group which is likely to be deteriorated by an acid or alkali coexists, the conventional hydrolyzing method using an acid or alkali often cannot be applied. For this reason, several improved methods have been developed.

For example, a method using ammonia in water-containing methanol is described in Tetrahedron Letters, p. 4273 (1968). A method using a large excess of butylamine is described in Tetrahedron Letters, p. 2263 (1986). A method using methyl-lithium is described in Journal of Orqanic Chemistry, Vol. 44, p. 2053 (1979). In addition, details of a cleavage method of similar esters are described in, for example, J.F.W. McOMIE ed., Protective Groups in Organic Chemistry, Plenum Press (NY) (London) (1973) and T.W. Greene, Protective Groups in Organic Synthesis, Willey Interscience (NY) (1981).

Although the above improved methods are useful in some cases, all the deacylating agents used in the methods are grouped into the category of "high nucleophilic agent and strong base" and, therefore, inevitably suffer from disadvantages. For example, in the aminolysis method, a large excess of amines is needed (10 equivalents in the literature). Thus, when a molecule contains, for example, a carbonyl group, a Schiff base is readily formed, and when a readily releasable group, such as a halogen atom, is present, a substitution reaction and a releasing reaction occur competitively.

In recent years, a highly selective organic reaction under mild conditions (neutral conditions) has been greatly desired. In view of this need, the above improved methods are not always satisfactory; a method of selectively cleaving the ester group under mild conditions without adversely affecting other functional groups has not been developed.

N-methyl-α-dialkylaminoacetohydroxamic acid compounds are described in Tetrahedron Letters, No 8, pp. 643-646 (1974) and Tetrahedron Letters, Vol. 30, No. 2, pp. 207-210 (1989). However, immobilization of the compounds onto insoluble polymers has not been reported.

SUMMARY OF THE INVENTION

An object of the present invention is to provide a deacylating agent capable of cleaving and releasing an acyl group or its homolog under substantially neutral conditions without adversely affecting other functional groups.

Another object of the present invention is to provide a deacylating agent which, when used in a deacylation reaction, can be separated from the reaction product only by filtration after the completion of the deacylation reaction.

Another object of the present invention is to provide a deacylating method using the deacylating agent of the present invention.

Accordingly the present invention provides a deacylating agent represented by the formula (I) as shown below and a deacylating method using the deacylating agent:

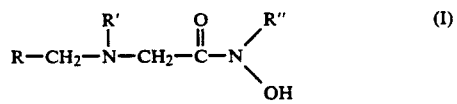

wherein R represents an insoluble polymer substituent, and R' and R" each represents an alkyl group.

DETAILED DESCRIPTION OF THE INVENTION

Figure 1:
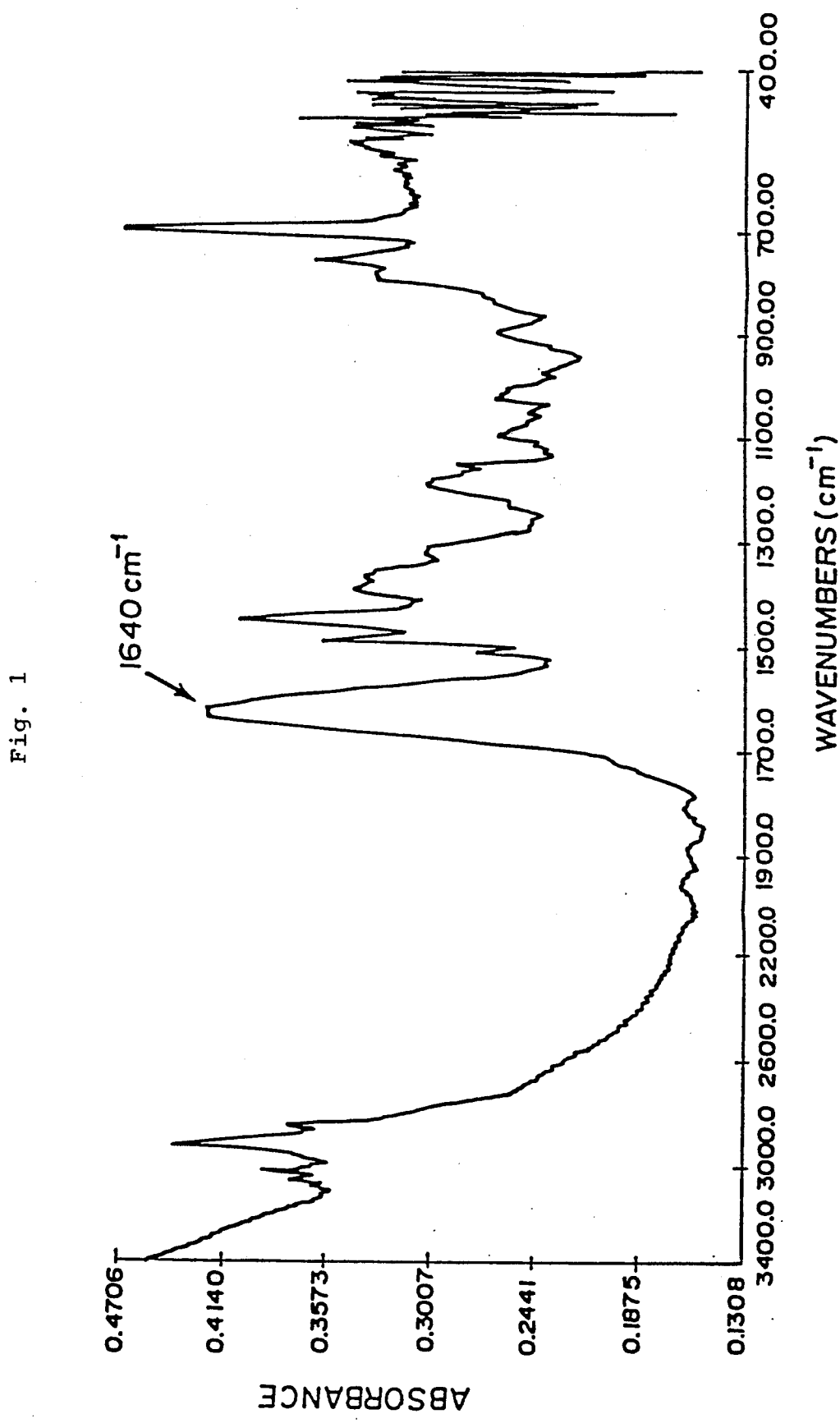
FIG. 1 is a graph showing an FT/IR spectrum of the compound (1) shown below in the synthesis scheme.

The term "insoluble" as used herein means that the polymer is insoluble in a solvent used in the deacylation reaction and with a deacylated compound.

The particular polymer main chain is not critical; however, preferably the polymer is cross-linked. The degree of cross-linking of the polymer is preferably 1 to 10% and particularly preferably 3 to 6%. A preferred example of the insoluble polymer is an insoluble polymer obtained by the copolymerization of styrene and divinylbenzene or methacrylamide and methylenebisacrylamide.

The copolymerization ratio of styrene and divinylbenzene is such that styrene/divinylbenzene is 99/1 to 90/10 (molar ratio). Particularly preferred for styrene/divinylbenzene is 96/4.

Preferably, R' and R" each represents an alkyl group having 1 to 4 carbon atoms.

The alkyl group may be straight or branched. Preferably, it is a methyl group or an ethyl group.

Examples of the deacylating agents of the present invention are shown below, although the present invention should not be construed as being limited thereto. In the examples, R has the same meaning as above.

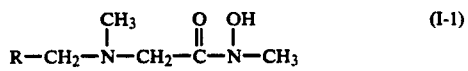

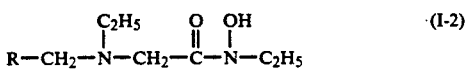

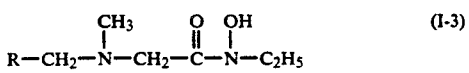

-continued $$\underset{(I-4)}{R-CH_2-\overset{\overset{C_2H_5}{|}}{N}-CH_2-\overset{\overset{O}{\|}}{C}-\overset{\overset{OH}{|}}{N}-CH_3}$$

The method of synthesizing the decylating agent of the present invention will be explained hereinafter, although the present invention is not limited thereto.

Scheme of Synthesis

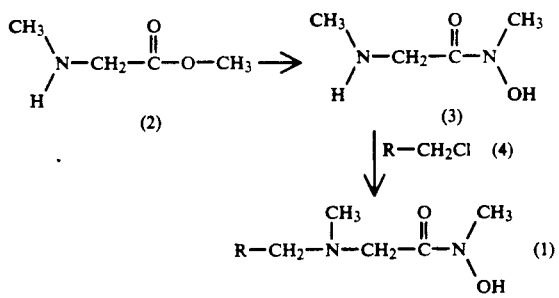

Synthesis of Compound (3)

21 g (0.48 mol) of NaOH was dissolved in a mixed 21 g (0.48 mol) of NaOH was dissolved in a mixed solvent of 100 ml of water and 50 ml of methanol, and 40 g (0.48 mol) of N-methylhydroxyamine hydrochloric acid salt was added thereto. The resulting mixture was stirred while cooling. After 30 minutes, 25 g (0.24 mol) of the compound (2) (sarcosine methyl ester, which is a commercially available product) was added. The resulting mixture was stirred, and after plugging, allowed to stand at room temperature for 4 days. The solvent was distilled away under reduced pressure to obtain a white residue. To this residue, 200 ml of methanol was added, and after being stirred well, the insoluble material was removed by filtration. The resulting filtrate was distilled under reduced pressure to obtain a residue. To this residue was added 300 ml of acetone, which was then stirred while heating and filtered. The filtrate was distilled under reduced pressure to obtain an oily material. Upon recrystallization of the oily material from an acetone/ether mixture, the compound (3) was obtained as white crystals in an amount of 26 g.

Synthesis of Compound (1)

As the compound (4), 5 g of a copolymer of styrene and divinylbenzene chloromethylated at the paraposition (sold under the name of Bio-Beads S-Xl, 200 to 400 mesh, potency: 4.15 meq/g, produced by Bio Rad Laboratory Corp.) was used. This compound was swollen by being placed in 50 ml of benzene. Then, a solution of 9.4 g (0.03 mol) of the compound (3) in 50 ml of methanol was added thereto, and the resulting mixture was stirred at room temperature for 2 days.

The reaction mixture was filtered. The beads were consecutively washed well with benzene, methanol, water and methanol benzene and then dried, whereupon 4.7 g of white beads were obtained.

Figure 2:
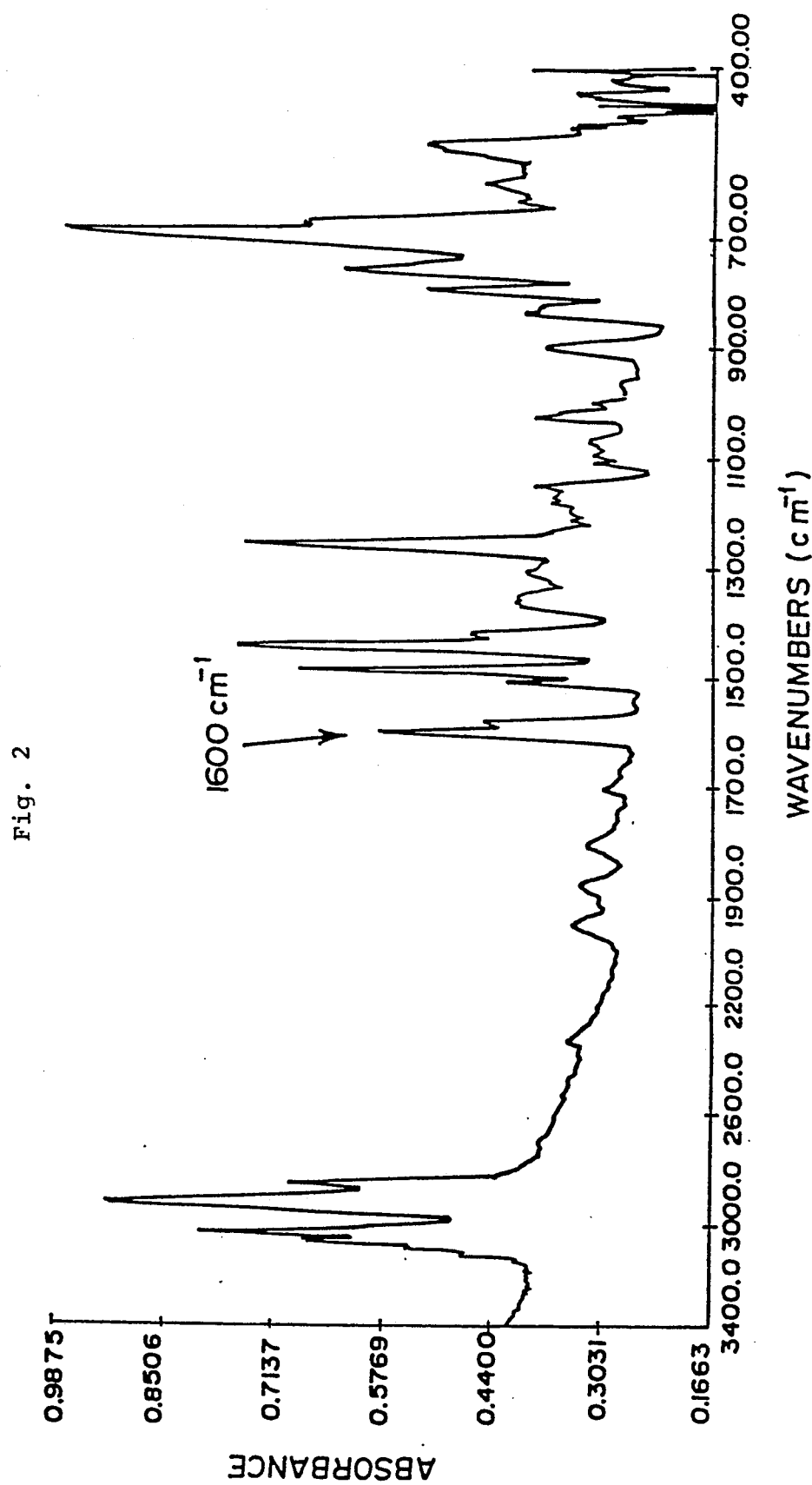
FIG. 2 is a graph showing an FT/IR spectrum of Bio-Beads S-Xl used as the compound (4) shown below in the synthesis scheme.

FIG. 1 shows the FT/IR spectrum (KBr method) of Compound (1) and FIG. 2 shows the FT/IR spectrum (KBr method) of Bio-Beads S-Xl used as Compound (4). By comparing FIG. 1 with FIG. 2, one can see that the hydroxamic acid is linked because a carbonyl absorption peak due to

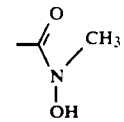

is observed at 1640 cm$^{-1}$.

The hydroxamic acid content as determined with a calibration curve by a method using FT/IR was 2.5 meq/g.

A compound having an acyl component readily subject to cleavage by a deacylating agent represented by the formula (I), or a vinylogous acylating component, is represented by the formula (II).

$$R_1-X-(C\!=\!\overset{\overset{R_3}{|}}{Z})_n-W-R_2 \qquad (II)$$

wherein X represents a hetero atom, preferably an oxygen atom, a nitrogen atom, or a sulfur atom; Z represents a carbon atom or a nitrogen atom, such that when X represents a nitrogen atom, or when Z represents a carbon atom, the compound has a substituent at the nitrogen atom or the carbon atom; W represents a carbonyl group or a sulfonyl group; $R_1$, $R_2$ and $R_3$ represent suitable organic groups (e.g., an alkyl group, an aromatic group), and $R_1$, $R_2$ and $R_3$ may be linked to one another; and n represents 0 or an integer Of 1 to 3, preferably 0 or an interger of 1 to 2.

Among the compounds represented by the formula (II), those containing a fragment $R_1-X-$ in which the pKa value of the product $R_1-X-H$ after cleavage, or the pKa value of the conjugated acid of $R_1-X^{\ominus}$, is not more than 10 are preferably used in the present invention.

The pKa used in the present invention, i.e., the reciprocal of the logarithm of the acid dissolution constant, is determined according to the method described in Michinori Ohki, *Acid and Base*, Baifukan, Japan (1976), pp. 15-20 unless otherwise indicated. That is, a fragment $RI-X-$ having a pKa of not more than 10 in the present invention is indicated by a compound containing a fragment $R_1-X-$ having an apparent pKa value of not more than 10 as obtained by the measuring method shown below.

As a solvent, a solution of water/ethanol in a ratio of ¼, or water/tetrahydrofuran in a ratio of ¼, is used, and the concentration of the compound represented by the formula (II) is controlled to (1) $1\times10^{-2}$ mol, (2) $1\times10^{-4}$ mol, or (3) $1\times10^{-6}$ mol. Using 2N HCl and 2N NaOH and a Type GT-05 automatic titrator (manufactured by Mitsubishi Kasei Corp.), the pKa measurement was carried out. Based on the pKa values at the three points (1), (2) and (3), listed above, an apparent pKa is determined by extrapolating to a value at a concentration of 0 by a calibration method.

In the present invention, the deacylation of a compound to be deacylated is carried out by mixing a deacylating agent of the formula (I) of the present invention and a compound to be deacylated (e.g. a compound of the formula (II)) so that they can react.

The conditions for the deacylation method of the present invention are not critical. The deacylating agent of the present invention is used in an amount of at least chemical equivalent to that of the compound to be deacylated. Usually the deacylation is fully achieved by using 3 equivalents or less of the deacylating compound per equivalent of the compound to be deacylated. As the reaction solvent, a non-aqueous solvent, such as THF, dioxane, DMF, CHCl₃, acetonitrile benzene or toluene can be used. To this non-aqueous solvent, a small amount of alcohol or water (about 1/10 to 1/50 by volume) is added. The compound to be deacylated may be added to a solution obtained by dissolving the deacylating agent of the present invention in the non-aqueous solvent, or the deacylating compound may be added to a solution obtained by dissolving the compound to be deacylated in the non-aqueous solvent. The reaction temperature is not critical; although a temperature of from room temperature to reflux temperature is preferably employed. It is desirable to carry out the reaction with stirring. Usually, the deacylation reaction is completed in 10 minutes to one day. After the completion of the reaction, the organic layer is filtered (in this operation, the deacylating agent is removed by filtration). The organic layer is dried and then distilled away. The residue is recrystallized from a suitable solvent (e.g., ether, n-hexane) or purified by column chromatography to obtain the desired product.

The compound of the present invention is useful for deacylating esters under substantially neutral conditions in an organic solvent. This deacylation is a means for releasing a protective group in the synthesis of medicines, or for releasing a reagent from a precursor of a photographic reagent. JP-A-59-198453 (the term "JP-A" as used herein means an "unexamined published Japanese patent application") and *Tetrahedron Letters*, No. 41, p. 3613–3616 (1974) disclose that N-alkylhydroxamic acid compounds exhibit high nucleophilic properties in the state that is dissociated in a solution having a pH of at least 10 or in a special reaction system such as a micelle system.

In these cases, however, high pH conditions or a special reaction system which is unsuitable for ordinary organic synthesis is needed. Moreover, if an alkali metal salt is used to release hydroxamic acid, it is insoluble in an organic solvent, and thus its use as a nucleophilic agent in a substantially organic solvent is limited.

The compound of the present invention overcomes the above problems. By introducing an alkylamino group in a suitable position in the molecule, it becomes possible to withdraw hydrogen from the molecule, and an active site of hydroxamic acid is produced.

The major advantage is that an insoluble polymer to which an active species is linked can be separated from the product only by a filtration after the reaction. The polymer in the present invention is placed in a glass tube, and a starting material is introduced into the glass tube from the top. Then, the product comes out from the bottom of the tube. Thus, the effect of the present invention is advantageous in that a clean and mass production reaction is realized.

The present invention is described in greater detail with reference to the following examples which are not meant to be limiting.

EXAMPLE

Deacylating agents of the formula (I) of the present invention and compounds to be deacylated of the general formula (II) were reacted under the combinations and conditions (reaction conditions, reaction temperature, and reaction solvent) shown in Table 1. Deacylation in the yield shown in Table 1 was attained.

TABLE

| Entry | Compound to be Deacylated | Mole Number of (I) | Solvent | Temperature (°C.) | Time (Hours) | Yield$^a$ (%) | |
|---|---|---|---|---|---|---|---|
| 1 | 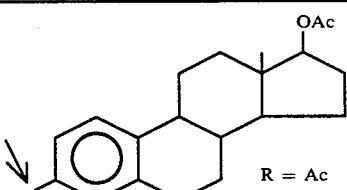 | 2.5 | CH₃OH | 45 | 3 | (R = H; m.p. 215–217° C.) | 78 |
| 2 | 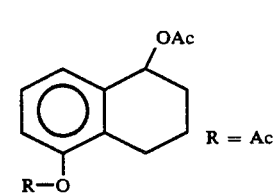 | 5.0 | THF/buffer$^b$ (1:1) | 45 | 4 | (R = H; m.p. 66° C.) | 83 |
| 3 | 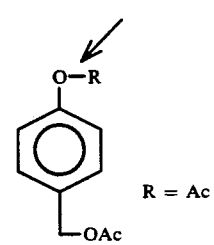 | 5.0 | CH₃OH | 50 | 1.5 | (R = H; oil) | 81 |

TABLE-continued

| Entry | Compound to be Deacylated | Mole Number of (1) | Solvent | Temperature (°C.) | Time (Hours) | Yield[a] (%) | |
|---|---|---|---|---|---|---|---|
| 4 | [structure: coumarin with CO$_2$Et, Cl, and R—O, R = Ac] (7) | 1.0 | THF/buffer (2:1) | Room Temp. | 1 | (R = H; oil 235-237° C.) | 98 |
| 5 | [structure: naphthalene with O—R, CO$_2$Ph, NHCOCF$_3$, R = Ac] | 2.5 | THF/buffer (1:1) | Room Temp. | 1 | (R = H; m.p. 175-177° C.) | 93 |
| 6 | [structure: benzene with O—R, Cl, H$_3$C, CH$_3$, OAc, R = Ac] | 5.0 | THF/buffer (3:1) | 45 | 2 | (R = H; m.p. 82-83° C.) | 84 |
| 7 | [structure: phenyl with O—R, NHCOCH$_3$, R = Ac] | 3.0 | EtOH | 45 | 1 | (R = H; m.p. 158-160° C.) | 78 |
| 8 | [structure: oxime with H, N—O—R, OCH$_3$, H$_3$CO, R = Ac] | 2.5 | THF/CH$_3$OH/ buffer (5:1:5) | 50 | 2 | (R = H; m.p. 108-110° C.) | 81 |
| 9 | [structure: H$_3$C—C(O—R)=CH—C(O)OEt, R = Ac] | 2.5 | EtOH | Room Temp. | 2 | (R = H; oil) | 90 |
| 10 | [structure: phenyl-triazole-S-CH with phthalide] | 2.0 | THF/DMF/ buffer (3:1:1) | 40 | 3 | (SH group structure: Ph—N, N, N=N; m.p. 154-157° C.) | 85 |

(The arrow indicates a bond undergoing selective cleavage.)

(The arrow indicates a bond portion undergoing selective cleavage.)
[a]Yield after purification
[b]0.1 M phosphate buffer (pH = 7.6)

While the invention has been described in detail and with reference to specific embodiments thereof, it will be apparent to one skilled in the art that various changes and modifications can be made therein without departing from the spirit and scope thereof.

What is claimed is:

1. A deacylating method comprising deacylating a substrate with a deacylating agent represented by formula (I):

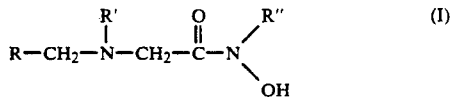

wherein R represents an insoluble polymer obtained by the copolymerization of styrene and divinylbenzend, and R' and R'' each represent an alkyl group; wherein said substrate is represented by formula (II):

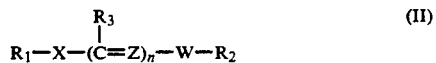

wherein X represents a hetero atom; Z represents a carbon atom or a nitrogen atom, such that when X represents a nitrogen atom, or when Z represents a carbon atom, the compound has a substituent at a nitrogen atom or a carbon atom; W represents a carbonyl group or a sulfonyl group; $R_1 R_2$, and $R_3$ represent organic groups, and $R_1$, $R_2$, and $R_3$ may be linked to one another; and n represents 0, 1, 2 or 3; and, wherein the deacylating is conducted in a non-aqueous solvent which contains a small amount of alcohol or water.

2. A deacylating method as claimed in claim 1, wherein X is selected from the group consisting of an oxygen atom, a nitrogen atom and a sulfur atom.

3. A deacylating method as claimed in claim 1, wherein n represents 0, 1, or 2.

4. A deacylating method as claimed in claim 1, wherein said compound represented by the formula (II) contains a fragment $R_1-X-$ which is cleaved such that a product $R_1-X-H$ having a pKa value of at most 10 is formed.

5. A deacylating method as claimed in claim 1, wherein said compound represented by the formula (II) contains a fragment $R_1-X-$ such that a conjugated acid of $R_1-X_1^{63}$ has a pKa value of at most 10.

6. A deacylating method as claimed in claim 1, wherein $R_1$, $R_2$ and $R_3$ each represent an alkyl or aromatic group.

* * * * *